United States Patent
Bristol (10) Patent No.: US 6,812,708 B2
(45) Date of Patent: Nov. 2, 2004

(54) COMBUSTIBLE-GAS MEASURING INSTRUMENT

(75) Inventor: L. Rodney Bristol, Chalfont, PA (US)

(73) Assignee: Scott Technologies, Inc., Beachwood, OH (US)

( * ) Notice: Subject to any disclaimer, the term of this patent is extended or adjusted under 35 U.S.C. 154(b) by 0 days.

(21) Appl. No.: 10/454,987

(22) Filed: Jun. 4, 2003

(65) Prior Publication Data
US 2004/0065140 A1 Apr. 8, 2004

Related U.S. Application Data (60) Provisional application No. 60/385,666, filed on Jun. 4, 2002.

(51) Int. Cl.$^7$ ........................... G01R 27/08; G01R 27/02
(52) U.S. Cl. ........................ 324/431; 324/439; 324/443; 73/25.05; 340/633
(58) Field of Search ................................ 324/431, 439, 324/441, 443, 444, 703, 706, 721, 725; 340/632, 633; 422/94–97; 73/21.05; 702/133

(56) References Cited

U.S. PATENT DOCUMENTS

| | | | |
|---|---|---|---|
| 3,607,084 A | 9/1971 | Mackey et al. | 436/152 |
| 3,906,721 A | 9/1975 | Micheli et al. | 60/276 |
| 4,305,724 A | 12/1981 | Micko | 436/56 |
| 4,441,981 A | 4/1984 | Okamoto et al. | 204/426 |
| 4,541,988 A | 9/1985 | Tozier et al. | 422/94 |
| 4,620,437 A | 11/1986 | Takami et al. | 73/31.05 |
| 4,786,476 A | 11/1988 | Munakata et al. | 422/98 |
| 4,818,977 A * | 4/1989 | Alexander | 340/633 |
| 4,854,155 A * | 8/1989 | Poli | 73/31.05 |
| 5,055,269 A | 10/1991 | Palumbo et al. | 422/96 |
| 5,549,871 A | 8/1996 | Kocache et al. | 422/95 |
| 5,780,715 A | 7/1998 | Imblum | 73/23.21 |
| 5,804,703 A | 9/1998 | Wind et al. | 73/25.01 |
| 5,844,122 A | 12/1998 | Kato | 73/1.06 |
| 5,902,556 A | 5/1999 | Van De Vyver et al. | 422/74 |
| 5,922,287 A | 7/1999 | Kato et al. | 422/95 |
| 6,336,354 B1 | 1/2002 | Suzuki et al. | 73/31.05 |
| 6,395,230 B1 | 5/2002 | Guerin et al. | 422/88 |
| 6,482,650 B1 | 11/2002 | Kato et al. | 436/37 |

* cited by examiner

Primary Examiner—Vincent Q. Nguyen
(74) Attorney, Agent, or Firm—Hodgson Russ LLP (57) ABSTRACT

A gas detection sensor system including active and reference elements ($R_{sense}$, $R_{ref}$) are arranged in a modified bridge circuit (12, 14, 22, 24) which allows power ($V_{bat}$) to be supplied seperately to the active and reference element ($R_{sense}$, $R_{ref}$). A digal processor (30) monitors the resistances of the elements ($R_{sense}$, $R_{ref}$) to control a pulse-width modulator supplying power to the elements, thereby maintaining nearly constant temperatures in the sensor elements ($R_{sense}$, $R_{ref}$) and to translate the decrease in power needed to maintain constant temperature on the catalytic element into an output proportional to the concentration of combutible gas in air. The system periodically measures the resistance of the elements (Rref, Rsense) and enables dual operating modes of catalytic-bead detector. One active or reference element ($R_{sense}$, $R_{ref}$) can alternately measure low concentrations of combustible gases up to the lower explosive limit (LEL) or measure high concentrations, up to 100% by volume.

30 Claims, 3 Drawing Sheets

COMBUSTIBLE-GAS MEASURING INSTRUMENT

CROSS REFERENCE TO A RELATED APPLICATION

Applicant claims priority based on U.S. Provisional Patent Application No. 60/385,666 filed Jun. 4, 2002 and entitled "Combustible-Gas Measuring Instrument" which is incorporated herein by reference.

BACKGROUND OF THE INVENTION

This invention relates to the art of gas detection sensors, and more particularly to a new and improved gas detector for combustible gas, using catalytic combustion and/or direct thermal effects, operating the sensor at constant temperature.

Catalytic gas detection sensors are basically temperature-sensitive resistors. A catalyst, typically platinum or platinum alloy, is heated by a resistor. The combination of resistor and catalyst may be called a catalytic element or sensing element. It may take many forms, including a filament, a spheroid, or a planar resistor on a suitable substrate. The spheroid form is often referred to as a "catalytic bead". The hot catalyst induces oxidation of combustible gas in air, generally without producing a flame. The oxidation heats the catalyst and the resistor further. The increased temperature increases the electrical resistance of the resistor. Increasing resistance corresponds to increasing concentrations of combustible gas.

However, as one can readily understand, anything that causes the temperature of the catalytic element to increase will be interpreted as an increase in the amount of combustible gas in the air. Likewise, anything that causes the temperature of the catalytic element to decrease will be interpreted as a decrease in the amount of combustible gas in the air.

In order to prevent changes in the temperature of the air or gas stream which is being monitored from causing a change which would be falsely interpreted as a change in the concentration of combustible gas in the air or gas stream, catalytic gas detection sensors usually include a reference element. The reference element is constructed nearly identically to the catalytic element except that the surface has reduced chemical activity from that of the catalytic element, but essentially equal thermal properties. The reduced chemical activity may be produced by "poisoning" the catalyst by various methods, such as adding small amounts of lead. In operation, the two elements are exposed to the same air or gas stream and the temperature of the difference between the elements generates the output signal.

In traditional gas detection instruments, the active or catalytic element and the reference are each connected in series across a suitable voltage supply. Another pair of fixed resistors are also connected in series across the same supply. The four resistances thus form a Wheatstone bridge. This configuration compensates for temperature changes not produced by oxidizing combustible gas. Voltage measured between the two voltage dividers of the Wheatstone bridge corresponds to combustible gas concentration. In some instruments, the supply and measurement terminals of the Wheatstone bridge are interchanged, where the catalytic element and the reference element are each connected in series with a fixed load resistor across the voltage supply. One disadvantage of traditional instruments is that sensor life is shortened by the increased temperature resulting from exposure to combustible gas. In some cases, the sensor may by destroyed by a single application of a high concentration of combustible gas. Conventional instruments also consume substantial energy beyond that required to heat the sensor elements, because of the need to maintain a stable voltage supply in the face of changing battery voltage.

The lower explosive limit (LEL) is a threshold concentration at and above which a combustible gas presents a danger of explosion. For example, the LEL of methane in air is about 5% concentration by volume. To sense combustible gases at concentrations below the LEL, a temperature sensitive resistor may be coated with a platinum or other suitable catalyst and electrically heated to facilitate oxidation at the surface of the catalyst. In the presence of a mixture of combustible gas and air, the gas oxidizes, releasing heat, which heats the resistor.

Thus, as previously described, to mitigate the effects of ambient temperature, humidity and electrical instability, the typical catalytic-bead combustible-gas detector comprises a pair of temperature-sensitive resistors. One resistor of the pair, which may be designated "Rsense" is coated with an active catalyst. The other resistor, which may be designated "Rref", lacks the active catalyst. Catalytic oxidation of combustible gas heats Rsense. Lacking the catalyst, Rref is affected only slightly by moderate concentrations of combustible gas.

Figure 1:
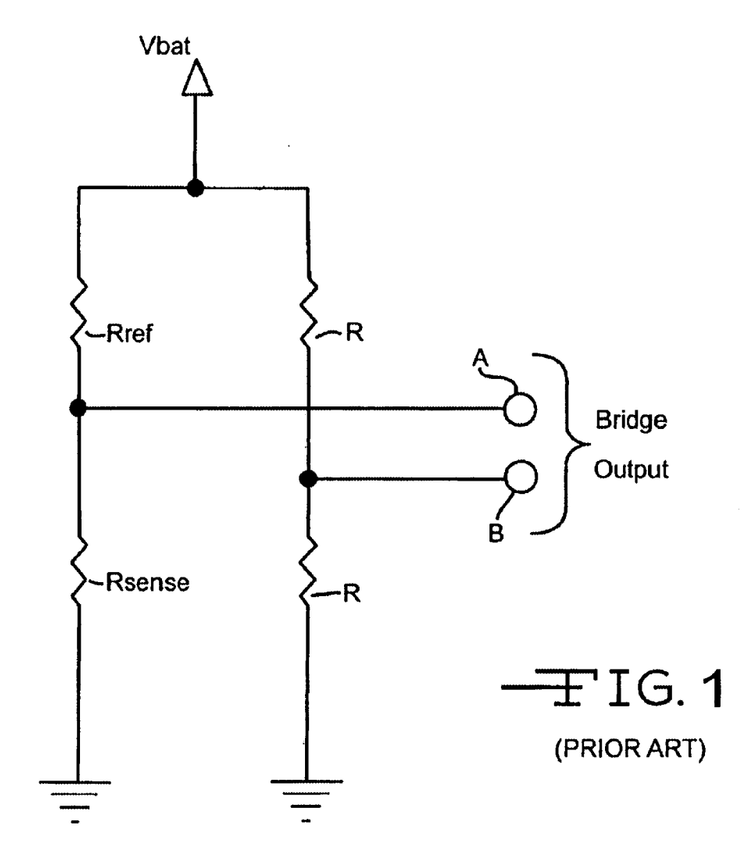
FIG. 1 is a schematic circuit diagram of a prior art catalytic sensor for detecting combustible gas.

In common practice, the pair of previously described temperature-sensitive resistors, Rref and Rsense, are connected in series, forming a voltage divider as shown in FIG. 1. This divider is arranged in a bridge circuit, where a fixed voltage divider comprising the series combination of resistors R and R nearly balances the divider formed by Rsense and Rref connected in series. The bridge is biased by a constant voltage Vbat. Low concentrations of combustible gas in air raise the temperature of Rsense, which raises its resistance. As a result, changes of gas concentration are indicated by changes in the bridge output voltage on terminals A and B, which is the difference between the voltages from the pair of dividers.

A cooling-effect sensor may be used to measure high concentrations of combustible gas. Such sensors exploit differing cooling effects of different gases in contact with a hot surface. Cooling of a hot surface depends on characteristic heat capacity, viscosity, and thermal conductivity of the gas in contact with the surface. The importance of each gas property may depend on the geometry of the hot surface and the geometry of structures affecting the convective movement of the gas across the surface. Polyatomic gases, those with molecules of three or more atoms, e.g. methane and other organic gases, have higher heat capacities than diatomic gases, such as oxygen and nitrogen (the major components of air). The heat capacity of any combustible, organic gas is about 1.2 times that of air. This greater heat capacity increases the convection cooling effect of a combustible gas (or any polyatomic gas) over that of air. Even though convection cooling effects may vary among various gases, the effect is reproducible for a given gas. In some literature, the cooling effect of combustible gases is referred to as "thermal conductivity."

Some prior art instruments have one sensor for measuring high concentrations of combustible gases and another sensor for measuring low (% LEL) concentrations. In some of these instruments, the high-concentration sensor is an oxygen sensor that determines the combustible gas concentration by measuring oxygen displacement. That method may result in falsely indicating a high concentration of combustible gas, because any gas, not necessarily combustible, would give the same effect. In other instruments, a cooling-effect sensor (described above) measures high concentrations of combustible gases. This method is generally better than oxygen displacement, because common, non-combustible gases have very similar cooling effects as air, so measurements are less ambiguous than measurements based on oxygen displacement. However, using one sensor to measure low concentrations and another sensor to measure high concentrations results in added cost and bulk.

SUMMARY OF THE INVENTION

The invention is directed to an instrument using a catalytic bead sensor to measure the concentrations of combustible gas in a space, such as a pipe carrying a mixture of gases. Improvements over prior art include enhanced reliability, extended range of measurement, and extended operation time in a battery-powered instrument. Advantages of constant-temperature operation of a catalytic-bead, combustible-gas sensor include avoiding detector failure with high concentrations of combustible gas, better linearity of measurement, reduced response time, and longer detector life. An advantage of pulse width modulation (PWM) for battery powered devices is conservation of energy, resulting in desirably longer run times between recharges or battery replacements than obtained with linear control. PWM control also may incur fewer components and simpler construction than switching regulators and other alternatives.

The invention combines the advantages of constant-temperature operation and PWM control for catalytic-bead, combustible-gas detectors. The invention arranges the active and reference elements of the gas sensor in a modified bridge circuit which allows power to be supplied, using pulse-width modulation, separately to the active and reference elements. An advantage is that constant temperature can be maintained on the elements by using a relatively inexpensive digital processor to control the pulse-width modulator, and to translate the decrease in power needed to maintain constant temperature on the catalytic element into an output proportional to the concentration of combustible gas in air. Thus, a system embodying the invention periodically measures the resistance of one or more sensor elements (Rref and Rsense) and controls the electrical bias applied to the elements, using PWM, thereby maintaining nearly constant temperatures in the sensor elements. Changes in gas concentrations are reflected in changing electrical bias. Another advantage is that the invention enables dual operating modes of catalytic-bead detectors. One sensor can alternately measure low concentrations of combustible gases up to the lower explosive limit (LEL) or measure high concentrations, up to 100% by volume.

The foregoing and additional advantages and characterizing features of the invention will become clearly apparent upon a reading of the ensuing detailed description together with the included drawings.

DETAILED DESCRIPTION OF THE INVENTION

Figure 2:
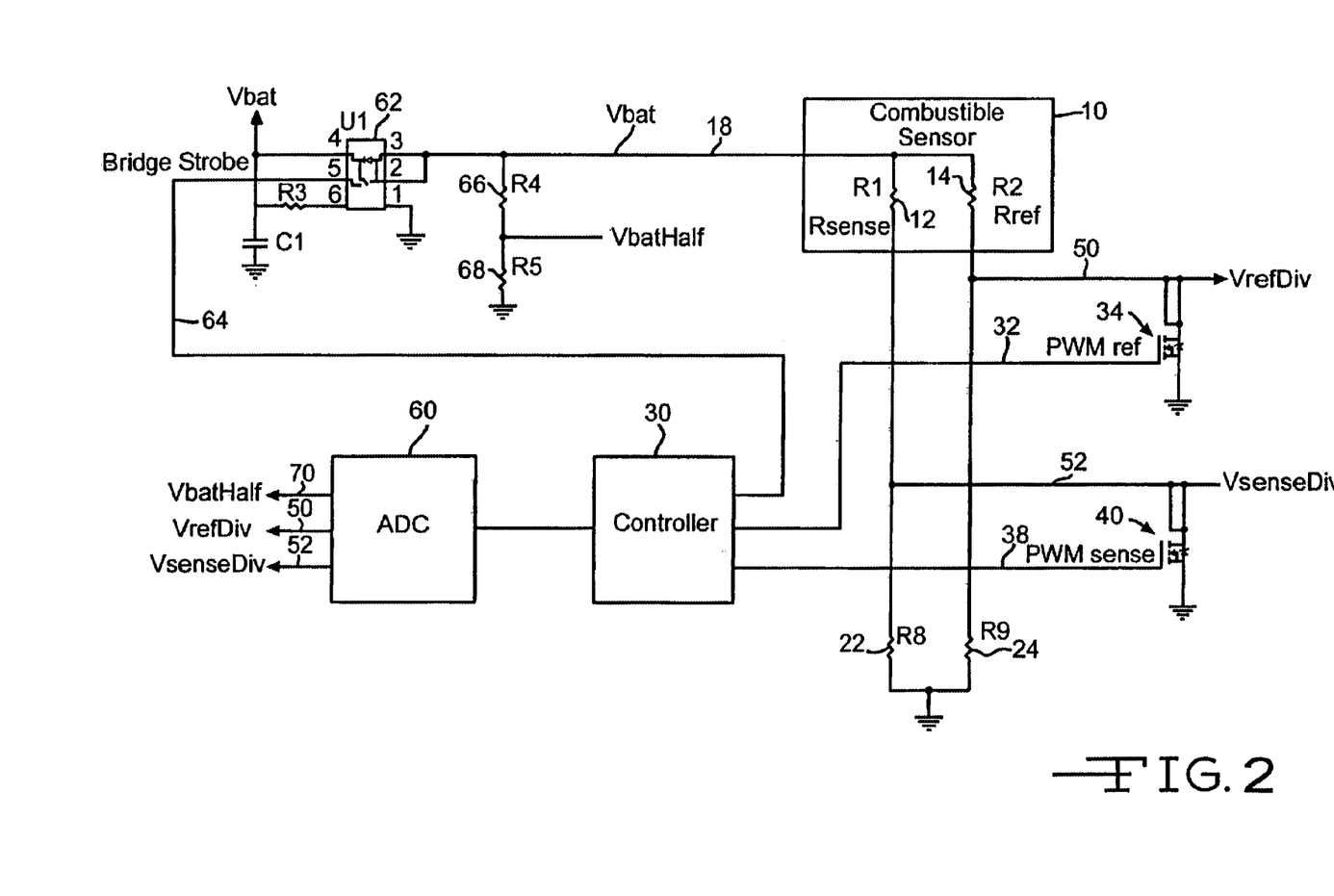
FIG. 2 is a schematic diagram illustrating the operation of the gas detector of the invention.

From time to time herein, reference may be made to FIG. 2, which is a schematic representation of an embodiment of the invention. The invention is not limited to the embodiment of FIG. 2. Further, the following description includes details that are meant to be illustrative of the invention, and should not be interpreted to limit the invention. Many other equivalent circuit topologies and circuit parameters can operate according to the invention.

In an embodiment of the invention, a sensor 10 includes two detector resistors 12 and 14 (Rsense and Rref) which have a common node 16 that is maintained at or periodically switched to a supply voltage (Vbat) on line 18. Rsense is series connected to a fixed load resistor 22 (RloadS), and Rref is series connected to another fixed load resistor 24 (RloadR), each series connection forming a voltage divider from Vbat, i.e. from node 16, to ground. Each of the fixed load resistors 22, 24 is periodically shorted by an FET, as driven by a PWM output from a controller. In particular, controller 30, which includes a processor, applies pulses designated PWMref on line 32 to the control terminal of a signal-controlled or voltage-controlled switch in the form of FET 34 which is connected from the junction of resistors 14 and 24 to ground. Similarly, controller 30 applies pulses designated PWMsense on line 38 to the control terminal of a signal-controlled or voltage-controlled switch in the form of FET 40 which connects from the junction of resistors 12 and 22 to ground. PWMref shorts the load resistor 24 associated with Rref (resistor 14), and PWMsense shorts the load resistor 22 associated with Rsense (resistor 12). When a load resistor is shorted, the full supply voltage (battery voltage) is applied to the resistor, Rsense or Rref, as the case may be. Between pulses of PWMref and PWMsense, when Rload (resistor 22 or 24) is not shorted by an FET 34 or 40, the respective voltage dividers provide voltages VrefDiv and VsenseDiv on lines 50 and 52, respectively. Each PWM signal is controlled as needed to keep Rsense and Rref at a predetermined resistance, this being done by a suitable program used by controller 30. Maintaining the resistance of Rsense and Rref maintains the temperature of each resistor.

Constant temperature corresponds to constant resistance of the temperature-dependent resistors, Rsense and Rref. Changes in gas concentration may be indicated by changes in the power provided to Rsense and Rref. For low concentrations, heat generated by catalytic combustion of detected gas at Rsense is offset by reducing its PWM drive to maintain its constant temperature. The reduction in electrical power resulting from reducing the PWM duty factor corresponds to the concentration of the detected gas. Higher concentrations of combustible-organic gases increase convection cooling of combustible-gas sensor Rref, which increases the electrical power required to maintain Rref at a constant temperature. The added power corresponds to the concentration of the gas.

For constant-temperature operation, according to the invention, each side of the sensor 10 is maintained at a constant resistance by regulating an associated pulse-width-modulated (PWM) driver. Constant temperature corresponds to constant resistance of the temperature-dependent resistors 12 and 14. The PWM on-off ratio on each side of the sensor, combined with battery voltage, determines a level of power. The circuit may be arranged so that the load resistor 22 or 24 alone does not conduct enough current to heat Rsense or Rref to the desired temperature. As a result, the PWM signal driving the FET can control the temperature of Rref and Rsense. The contribution of the load resistor to the mean-square-voltage on Rsense and on Rref may be taken into account to get accurate measurements.

Periodically and during the off time of each PWM, an analog-to-digital converter (ADC) 60 may be set to measure the voltages from Rref-RloadR and Rsense-RloadS, designated VrefDiv and VsenseDiv. At other times, it may measure the supply voltage, designated Vbat. The digital output of the ADC may be applied to controller 30. The controller 30, using any suitable program, automatically adjusts PWM-ref to maintain a constant ratio between VrefDiv and Vbat. It adjusts PWMsense to maintain a constant ratio between VsenseDiv and Vbat. Maintaining constant ratios of those voltages maintains constant resistances and temperatures of Rref and Rsense.

Vbat may be represented to the ADC by using a voltage divider comprising the series combination of resistors 66 and 68 connected between line 18 on which Vbat is present and ground, providing an output herein referred to as Vbathalf on line 70, although the value need not be 50% of Vbat. This fraction of Vbat (Vbathalf) may serve as the reference voltage for comparing with VsenseDiv, the voltage associated with Rsense, and VrefDiv, the voltage associated with Rref.

The program contained in controller 30 may calculate a first ratio, the ratio of Vbathalf to VrefDiv. It may also calculate a second ratio, the ratio of Vbathalf to VsenseDiv. Each of the first and second ratios is compared with a respective target or set point to adjust the associated PWM to maintain the first and second ratios nearly constant, which implies constant resistances of Rref and Rsense. A particular root-mean-square voltage will be characteristic of the bias controlled by each PWM signal as it maintains the associated divider-ratio at the associated target.

The target values are set to produce a desired root-mean-square voltage across each of Rref and Rsense with no combustible gas applied. The voltage-divider-ratio set point, which corresponds to the voltage without gas applied, also corresponds to a temperature with or without gas applied. Changes in the PWM signal maintaining the ratio of the divider ratios at the set point reflect changes in applied gas concentration.

Alternatively to the controller 30 calculating the ratios of VrefDiv-to-Vbathalf and VsenseDiv-to-Vbathalf, the ADC 60 may produce the ratios directly. The ADC 60 produces the ratios directly by being configured with VbatHalf as the ADC reference input during the times when it measures VrefDiv and VsenseDiv. As a ratiometric device, the ADC 60 provides successive outputs that are directly proportional to the two ratios, VrefDiv-to-Vbathalf and VsenseDiv-to-Vbathalf.

Two stages of control may protect Rsense from overheating in high concentrations of combustible gas. In the first stage, PWMsense maintains the desired temperature up to 100% LEL. When gas concentration rises further, PWM-sense can be shut down completely, then restored normal bias when gas concentration falls to a safe level.

The outputs of the detector voltage dividers may be applied to multiplexed inputs of an analog-to-digital converter (ADC) 60. For practical considerations, the ADC 60 may operate on a fixed supply voltage, lower than the battery voltage. Typically, an ADC measures input voltages in a range from its negative supply terminal voltage to its positive power-supply terminal voltage. Therefore, the ADC power supply and Rload may be chosen so the voltage divider outputs are within the ADC power supply range under all expected conditions of battery charge, when the detector is operating at the desired temperature. Where advantageous to the system design, the connections to Vbat and Gnd may be interchanged, so the ADC input is the voltage across the sensor elements (Rref and Rsense) instead of Rload(s). A fixed voltage divider presents a fraction of the battery voltage (VbatHalf) to the ADC, within its input voltage range.

A programmable, digital controller 30, such as a Texas Instruments MSP430f149, may operate the ADC 60, process the ADC outputs, or control the PWM signals. The ADC and PWMs may be embedded in the controller. The following discussion assumes the ADC and PWMs are embedded in the controller.

Each of the pair of fixed load resistors 22 and 24 may be periodically shorted by a switching device, such as each FET 34 and 40, as driven by a PWM signal from the controller 30. When the fixed load resistor is shorted, nearly the full battery voltage is applied to Rref or Rsense. By executing a suitable program, which modulates the signal driving the FET, in response to the signals applied to the ADC, the controller 30 maintains the resistance of each sensor element 12 and 14. Each PWM signal is modulated as needed to force Rsense and Rref (resistors 12 and 14) to a predetermined resistance. Maintaining the resistance of each sensor element maintains a constant temperature of each sensor element. The contribution of the load resistor to the mean-square-voltage on each sensor element may be taken into account to get accurate measurements. To assure that the PWM can control sensor-element temperature, the circuit may be designed so that the load resistor alone cannot conduct enough current to heat the element to the desired temperature.

In an embodiment of the invention, a battery voltage, designated Vbat, may be applied to a node to which three voltage dividers are connected. As such, Vbat drives a reference voltage divider, for example Vbat applied to $R_4$ and $R_5$ (resistors 66 and 68) to ground. Vbathalf on line 70 is supplied from between $R_4$ and $R_5$ to the ADC. Vbat also drives two gas detector voltage dividers (discussed above), one comprising Vbat applied to $R_2$, $R_9$ (resistor 14, resistor 24) to ground, and the other comprising Vbat applied to $R_1$, $R_8$ (resistor 12, resistor 22) to ground. By way of example, in an illustrative gas detecting apparatus, the resistance of each resistor $R_8$ and $R_9$ may be 54.9 ohms and the resistance of each element Rref and Rsense, when operating at a desired temperature, may be 47.5 ohms.

Figure 3:
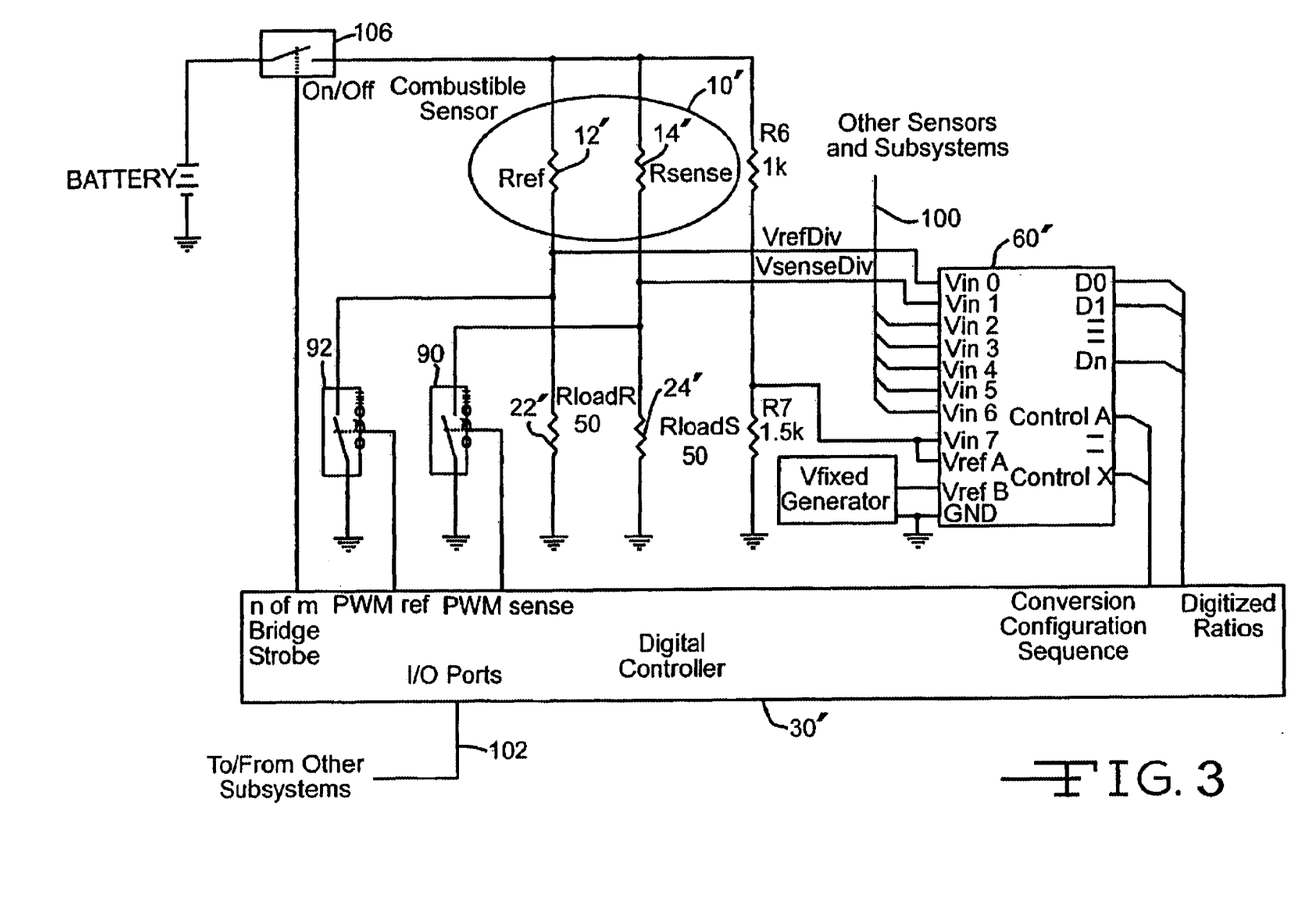
FIG. 3 is a schematic diagram further illustrating the gas detector of the invention.

By way of further illustration, FIG. 3 presents a somewhat simplified presentation of the system of FIG. 2. Sensor 10' includes resistors 12' (Rref) and 14' (Rsense) and load resistors 22' and 24' are connected between resistors 12' and 14', respectively, and ground. The FETs 34 and 40 of FIG. 2 are represented in FIG. 3 as the voltage or signal controlled switches 90 and 92, respectively. A digital controller 30' and ADC 60' are shown. Other inputs from portions of the apparatus of which sensor 10' is a part can be supplied to ADC via a bus 100. Similarly, bus 102 connects these other portions of the apparatus to controller 30'.

There is an on/off switch 106 which controls the voltage applied to both the reference and the catalytic element. There are two pulse-width modulation switch functions, labeled PWM ref and PWM sense. Both switches 90 and 92 are controlled by the digital controller 30' and both switches are used to deliver pulses of power to the active and reference elements 12' and 14', respectively. Overall control is provided by the switch 106 in series with the battery. This switch applies power to the catalytic element and the reference element simultaneously. The switch may be cycled rapidly to compensate for changes in battery voltage. The switching cycle may be chosen to maintain the condition that the currents through resistors 22' and 24' are insufficient to heat sensor resistors 10' and 12' to their predetermined, desired temperatures and also maintain the condition that switches 90 and 92, can be controlled by PWMref and PWMsense, respectively, to add sufficient current heat sensor resistors 10' and 12' resistors to their desired temperatures. For example, the controller may operate switch 106 such that in a cycle of ten time intervals, switch 106 is on for four intervals and off for six. The number of intervals of the ten in a cycle that the switch is on are set as needed to keep sensor element temperatures under control of the PWMs, despite changes in battery voltage.

On switching from the catalytic mode, for measuring gas below LEL, to the cooling effect mode, for measuring gas concentrations above LEL, the controller 30' shuts down the on/off switch 106 briefly, to cool resistor 14', Rsense, below the temperature for catalytic activity. Then the controller resumes on/off switch 106 and PWM ref operation to reestablish and maintain the desired temperature in resistor 12', Rref. PWM sense is disabled in cooling effect mode.

Thus, FIGS. 2 and 3 illustrate how the invention has arranged the active and reference elements in a modified bridge circuit which allows power to be supplied, using pulse-width modulation, separately to the active and reference elements. FIGS. 2 and 3 illustrate the principles by which the invention supplies power pulses to the active and reference elements and by which the invention regulates those pulses to maintain constant resistance. The resistance is, in turn, proportional to their temperature. The pulses from the controller act to maintain a constant temperature on the active and catalytic elements.

The main advantage of the technique of the invention is that constant temperature can be maintained on the elements by using a relatively inexpensive digital processor to determine the resistance divider ratios to control the pulse-width modulator, and to translate the decrease in power needed to maintain constant temperature on the catalytic element into an output proportional to the concentration of combustible gas in air.

While pulse-width modulation is employed in the embodiment of the invention illustrated herein, the various modes of variable pulse width and/or frequency and/or pulse magnitude can be utilized.

There are limitations on the range of concentration of combustible gas in air that traditional catalytic sensors can accurately measure. When the traditional sensor is exposed to high concentrations of flammable gases or vapors in air, the sensor output may become unusable or erroneous, falsely indicating a safe environment. This is a result of an enriched fuel-air mixture that generates less heat than leaner mixtures. In addition, such sensors may be damaged by the extreme heat generated by catalytic combustion.

Additional protection may be provided against damaging the sensor by sensing rapid increases in gas concentration. It may be advantageous to switch from catalytic mode to cooling effect mode when indicated concentration is only 50% of the lower explosive limit (LEL), if the concentration is increasing rapidly.

When the catalytic element is shut down and the reference element is maintained at constant temperature, the sensor operates in the cooling effect mode. The rate at which the reference element loses heat is proportional to the amount of combustible gas in the air and is also a function of the particular combustible gas present. Therefore, an increase in the power necessary to keep the element at a constant temperature is proportional to the increase in the percentage of the combustible gas in the air. Because the reference element is now acting by itself, its indications can only be accurate so long as there is no substantial change in the physical parameters of the gas stream. The chief physical parameter is the temperature of the gas stream. However, relative humidity and barometric pressure can also affect the rate at which the gas stream removes heat from the reference element.

As a result of the above-described single element operation, the accuracy of the gas detection instrument can only be relied upon for a limited period of time after the catalytic element has been shut down and the reference element starts operating as a cooling effect sensor. This uncertainty may be reduced by use of an auxiliary temperature sensor, especially if the sensor is placed in the stream of gas under test. Pressure and humidity may be compensated as needed, using separate sensors.

Referring again to FIG. 2, by way of example, in an illustrative gas detecting apparatus, the ADC 60 may be configured to produce a data output according to the equation:

Output_data=2^N*Vin/Vref, where $N$ is the number of binary bits in the output data.

For a 12-bit ADC, the values given produce a specific analog-to-digital conversion result.

OutputData=4096*Vbat*54.9/(54.9+47.5)/(Vbat*1500/2500)= 4096*54.9/(54.9+47.5)/(1500/2500)=3660. Note that *Vbat* is immaterial to the result. (However, the ADC may not be accurate for extreme values of Vbat.)

This data may be used as a set point to maintain constant temperatures in the sensor resistors 14 (Rref) or 12 (Rsense). These set points will be referred to herein as DividerTargetRef and DividerTargetSense. In this example, the default value for set points DividerTargetRef and DividerTargetSense is 3660. The controller 30 adjusts the duty factors of PWMref and PWM sense to maintain the ADC output data, when measuring the resistor divider ratios respecting sensor resistors 14 (Rref) or 12 (Rsense), close to set points DividerTargetRef and DividerTargetSense. As part of setting up the gas detector, set points DividerTargetRef and DividerTargetSense may be adjusted, such that the controller 30 develops a particular desired mean-square voltage, such as 2.75 V, across Rsense and across Rref. As a result, Rsense may be made to operate near its optimum voltage.

Various means are available to determine the mean square voltage applied to the sensor resistors, 12 (Rsense) and 14 (Rref). In an embodiment, the mean square voltage is calculated from the PWM duty factors, the battery voltage, and the value of Rload (resistors 22 and 24).

If the analog-to-digital conversion result when measuring the resistor divider ratios respecting sensor resistors 14 (Rref) or 12 (Rsense) is less than corresponding set points DividerTargetRef or DividerTargetSense, the temperature of the corresponding sensor resistor 12 or 14 is too high, and the PWM control logic responds by reducing the PWM duty factor for that part of the sensor. When the conversion result exceeds the target, the controller 30 increases the duty factor to raise the temperature of that part of the sensor. Thus the average PWM duty factor holds each divider ratio near the target in order to maintain a constant temperature for each resistor 12 and 14 in the sensor.

The resolution required for measuring gas concentration may exceed the resolution of the PWM. The controller 30 may be programmed so the PWM duty factor oscillates around the ideal duty factor. Low-pass filters (not shown) may be provided to filter the oscillating duty factors in order to produce a time-weighted-average of the duty factor to enough resolution to yield the desired measurement resolution.

The load resistors 22 and 24 ($R_8$ and $R_9$) influence the power dissipated in the sensor resistors 12 and 14 (Rsense and Rref). When the driving FET is off, current continues to flow through the series combination of resistors 14 and 24, or current continues to flow through the series combination of resistors 12 and 22. These currents contribute to total power dissipated in Rsense and Rref. Both the FET-on and the FET-off contributors to Rsense and Rref dissipation should be included in the calculation of mean-square voltage and power. This effect varies with Vbat. With high values of Vbat, the FET-off condition, where Rsense or Rref current are determined by Rload S and Rload R, the reduced current could exceed the current required to attain the target temperature of Rsense or Rref. The BridgeStrobe signal, shown in FIG. 2 on line 64 between controller 30 and component 62 may work with the PWM to counter this. For example, when the duty factor needed to achieve the target temperature (resistance), falls too low, such as below 30%, the density of PWM cycles may be reduced by reducing the number of BridgeStrobes of a cycle of ten. When the needed duty factor exceeds about 80%, PWM cycle density may be increased. This maintains high energy efficiency, minimizes energy lost in the load resistors, and permits a wide range for Vbat.

In general: power=$V^2/R$, $V^2=PR$. As described above, electrical power changes are proportional to gas concentrations. Specifically, in a device according to the invention power in a sensor resistor, Rsense or Rref (generically referred to herein as Rt), may be determined by:

$$P=[Vbat^2*D/Rt+(Vbat*G)^2*(1-D)/Rt]*StrobeFactor, \quad [eq. 1]$$

where:

P=power in temperature-sensing resistor, which changes negatively in proportion to changes in combustible-gas concentration, Vbat=battery voltage, which may be 3<Vbat<4.9 V, D=PWM duty factor, which may be 0<D<1, Rt=resistance of temperature-sensing resistor, Rref or Rsense, G=divider ratio, Rt/(Rt+Rload), Rload=fixed load resistance, which may be 54.9 ohms, StrobeFactor=duty factor of BridgeStrobe, which may be 1, 0.9 . . . 0.2, 0.1.

Since the actual value of Rt is fixed by the operation of the PWM to maintain the divider ratio (G) at a constant value, changes in gas concentration are indicated by the following:

$$P=[Vbat^2*D/Rt+(Vbat*G)^2*(1-D)/Rt]*StrobeFactor, \quad [eq. 1]$$

$$PRt=Vbat^2*[D+G^2*(1-D)]*StrobeFactor, \quad [eq. 2]$$

=Vms applied to the sensor, which may be=$2.75^2$=7.5625, in clear air.

Rsense may respond to changing gas concentrations with changing power requirements, relative to the power needed to develop the operating temperature in air. The power (P, in watts) dissipated in Rsense, multiplied by the resistance (Rsense, in ohms) equals the mean square voltage (Vms, in volts) applied to Rsense.

$$Vms=Vbat^2[d+G^2(1-d)], \quad [eq. 3]$$

where

Vms=mean square voltage applied,

Vbat=battery voltage applied when PWM is driving, d=PWM duty factor,

G=fraction of Vbat applied to Rsense, via Rload, when PWM is off.

Since resistance is regulated to a constant by the PWM, power is proportional to Vms. Changes in Vms indicate changes in concentration of combustible gas.

The algorithms and software code for executing these calculations may be developed by widely accepted principles and methods of software engineering and programming. Such algorithms and code would be designed to meet the specific criteria of the instrument design, generally in such a way as to minimize the processor resources required, in combination with all other features and functions of the instrument. In addition, software in the digital processor will coordinate the PWMs and analog to digital converter described herein, according to the specific properties of such system elements, as thoroughly described in such documents as MSP430x1xx Family User's Guide, Texas Instruments Publication SLAU049A and data brochure for MSP430x13x, MSP430x14x MIXED SIGNAL MICROCONTROLLER, Texas Instruments Publication SLAS272C.

In general, zeroing the detector is the act of recording the output of a (gas) sensor with no stimulus (clear air). The recorded value obtained during zeroing is used to adjust responses from the detector in order to obtain a truer reading. For example, after the detector has been returned to service, the recorded value obtained during zeroing may be subtracted from detector responses to get truer readings. For convenience, the operating voltage of a combustible gas sensor may be normalized at the same time that zeroing occurs.

Sensors are constructed to minimize aging effects and environmental effects on their outputs. However, zeroing may be performed periodically in order to take account of the effects of sensor aging, as well as ambient temperature, and small instabilities in associated electronic circuits.

During zeroing, to assure predictable detector response to combustible gas, the standard operating voltage, such as 2.75 V, may be maintained in clear air. This may be established by applying eq. 2 (the Vms equation) and adjusting DividerTargetRef and DividerTargetSense as required to produce the standard operating voltage across the sensor resistors 14 (Rref) and 12 (Rsense). For example, a 2.75 V RMS operating point is equivalent to a mean square voltage (Vms) of 7.5625. The adjusted values of DividerTargetRef and DividerTargetSense may vary according to the properties of the individual sensor and resistor tolerances. The actual values may be determined by the following steps:

1. move the instrument to clear air, free of combustible gases;
2. use Vbat, PWM duty factor, currently active RxTarget, StrobeFactor, DividerTargetRef, and DividerTargetSense to calculate the Vms applied to each of the sensor resistors 14 (Rref) and 12 (Rsense);
3. compare the calculated values to the Vms corresponding to the standard operating voltage;
4. adjust DividerTargetRef and DividerTargetSense to produce Vms closer to the Vms corresponding to the standard operating voltage;
5. repeat steps 2–4 until a stable Vms results, acceptably close to the Vms corresponding to the standard operating voltage;

6. record DividerTargetRef and DividerTargetSense for future operation.

The preceding steps may be performed as part of the zeroing procedure. Subsequent operation may maintain the temperature of resistors 14 (Rref) and 12 (Rsense) the sensor, by keeping the resistances constant, by adjusting PWMref and PWMsense as needed.

In clear air during zeroing, the (small) difference between Vms across the sensor resistor 14 (Ref) and Vms across the sensor resistor 12 (Rsense) may be recorded as the offset, and used for subsequent gas-concentration measurements. The small difference will be the difference between the residual errors in setting Vms to the Vms corresponding to the standard operating voltage, via DividerTargetRef and DividerTargetSense Values, for the two sides of the sensor. Vms for Rref also may be recorded as the basis for high-concentration measurements, based on heat capacity, as described above.

Vms across the sensor resistor 14 (Rref) may be designated Vms Ref. Vms across the sensor resistor 12 (Rsense) may be designated VmsSense. Span calibration (catalytic) may determine what further difference between VmsSense and VmsRef results from exposing the sensor to calibration gas. VmsSense and VmsRef may be adjusted automatically by the resistance-regulation algorithm. Span calibration (cooling effect) exposes the sensor to a high-concentration calibration gas and determines how much VmsRef changes from the value of VmsRef recorded at sensor-zero in clear air. VmsRef may be adjusted automatically by the resistance-regulation algorithm.

Although embodiments of the invention have been described herein, the invention is not limited to such embodiments. The claims which follow are directed to the invention, and are intended to further describe the invention, but are not intended to limit the scope of the invention.

What is claimed is:

1. A gas detector comprising:
a) at least one active sensor element having electrical resistance and adapted to be located in fluid contact with a gas having constituents which can change;
b) a circuit including the active sensor element for supplying power to heat the sensor element;
c) means including a source of pulse modulation operatively connected to the circuit to control power to the active sensor element, the sensor element being composed such that the gas constituents when changing cause the temperature of the heated active sensor element to change;
d) means operatively connected to the active sensor element and in controlling relation to the source of pulse modulation to determine the resistance of the sensor element and to change the pulse modulation to maintain the sensor element at a constant temperature; and
e) means operatively associated with the resistance determining and pulse modulation changing means to relate the change in pulse modulation to a change in the composition of the gas being monitored.

2. The gas detector of claim 1, wherein the source of pulse modulation, the resistance determining and pulse modulation changing means and means relating modulation change to gas composition change are incorporated in a controller.

3. The gas detector of claim 1, further including another sensor element serving as a reference element having electrical resistance and adapted to be located in fluid contact with the gas, the reference element being composed such that the gas constituents when changing do not cause the temperature of the heated reference element to change as much as they change the temperature of the active element.

4. A gas detection method comprising:
a) providing at least one sensor element having electrical resistance and adapted to be located in fluid contact with a gas having constituents which can change;
b) supplying power to heat the sensor element;
c) utilizing pulse modulation to control power to the sensor element, the sensor element being composed such that the gas constituents when changing cause the temperature of the heated sensor element to change;
d) determining the resistance of the sensor element;
e) utilizing change in the resistance of the sensor element to change the pulse modulation to maintain the sensor element at a constant temperature; and
f) relating the change in pulse modulation to a change in the composition of the gas being measured.

5. A gas detector comprising:
a) an active sensor element and a reference sensor element each having electrical resistance and adapted to be located in fluid contact with a gas having constituents which can change;
b) a circuit including the active and reference sensor elements for supplying power to heat the sensor elements;
c) means including a source of pulse modulation operatively connected to the circuit to control power to the sensor elements, the active sensor element being composed such that the gas constituents when changing cause the temperature of the heated active sensor element to change and the reference sensor element being composed such that the gas constituents when changing do not cause the temperature of the heated reference sensor element to change as much as the gas constituents cause the temperature of the heated active element to change;
d) means operatively connected to the active and reference sensor elements and in controlling relation to the source of pulse modulation to determine the resistances of the active and reference sensor elements and to change the pulse modulation to maintain the active and reference sensor elements at a constant temperature; and
e) means operatively associated with the resistance determining and pulse modulation changing means to relate the change in pulse modulation to a change in the composition of the gas being monitored.

6. The gas detector of claim 5, wherein the means operatively associated with the resistance determining means and pulse modulation changing means utilizes the difference between the power supplied to the active sensor element and the power supplied to the reference sensor element to maintain the active and reference sensor elements to provide an indication of the change in composition of the gas being monitored.

7. The gas detector of claim 5, wherein the source of pulse modulation, the resistance determining and pulse modulation changing means and means relating modulation change to gas composition change are incorporated in a controller.

8. The gas detector of claim 5, further including:
a) means operatively connected to the active and reference sensor elements and in controlling relation to the source of pulse modulation to substantially reduce the supply of power to the active sensor element and continue powering the reference sensor element;

b) so that when the concentration of gas being detected reaches a predetermined level, the active sensor element is protected from overheating and the reference sensor element acts as a cooling-effect element, and the change in pulse modulation needed to keep the reference element at a constant temperature is related to the change in the composition of the gas being monitored.

9. A gas detection method comprising:

a) providing an active sensor element and a reference sensor element each having electrical resistance and adapted to be located in fluid contact with a gas having constituents which can change;

b) supplying power to heat the active and reference sensor elements;

c) utilizing pulse modulation to control power to the sensor elements, the active sensor element being composed such that the gas constituents when changing cause the temperature of the heated active sensor element to change and the reference sensor element being composed such that the gas constituents when changing do not cause the temperature of the heated reference sensor element to change as much as the gas constituents cause the temperature of the heated active sensor element to change;

d) determining the resistances of the sensor elements;

e) utilizing change in the resistances of the sensor elements to change the pulse modulation to maintain the sensor elements at a constant temperature; and f) relating the change in pulse modulation to a change in the composition of the gas being measured.

10. The gas detection method of claim 9, wherein the difference between the power delivered to the active sensor element and the power delivered to the reference sensor element to maintain the sensor elements at a constant temperature is related to a change in the composition of the gas being measured.

11. The gas detection method of claim 9 further including:

a) determining when the concentration of gas being detected reaches a predetermined level;

b) substantially reducing the supply of power to the active sensor element and continuing supply of power to the reference sensor element whereby the reference sensor element acts as a cooling-effect sensor; and c) relating the change in pulse modulation needed to keep the reference sensor element at a constant temperature to a change in composition of the gas being monitored.

12. A gas detector comprising:

a) a circuit operatively connected to a source of power and containing an active element and a reference element arranged in the circuit for separate current flow through the active and reference elements, the active element changing in temperature and resistance in the presence of the gas being detected; and b) a controller operatively connected to the circuit for controlling the supply of power, using pulse modulation, separately to the active and reference elements, the controller also being connected in monitoring relation to the active and reference elements to monitor the resistances of the active and reference elements, the resistances being proportional to the temperatures of the active and reference elements, and the controller using the resistances of the active and reference elements to control the pulse modulation to maintain a constant temperature on the active and reference elements.

13. The gas detector of claim 12, wherein the circuit includes a node to which bias voltage is applied, wherein the active element and a first load resistor are connected in series between the node and ground, and wherein the reference element and a second load resistor are connected in series between the node and ground.

14. The gas detector of claim 13, including:

a) a first signal controlled switch connected across first load resistor;

b) means for applying pulse modulation signals from the controller in controlling relation to the first signal controlled switch;

c) a second signal controlled switch connected across the second load resistor; and d) means for applying pulse modulation signals from the controller in controlling relation to the second signal controlled switch.

15. The gas detector of claim 14, including:

a) means for connecting the junction of the active element and first load resistor to the controller so that voltage associated with the active element can be read by the controller; and b) means for connecting the junction of the reference element and the second load resistor to the controller so that voltage associated with the reference element can be read by the controller.

16. The gas detector of claim 12, wherein the controller translates the difference in power supplied to the active and reference elements needed to maintain constant temperature on the active and reference elements into an output proportional to the concentration of gas being detected.

17. The gas detector according to claim 16, wherein the controller includes means for substantially reducing power applied to the active element while continuing to apply power to the reference element when the controller senses a rise in the concentration of gas being detected above a predetermined level.

18. The gas detector according to claim 17, wherein the controller includes means for determining the increase in power needed to maintain the reference element at a constant temperature as a measure of the concentration of the gas being detected.

19. A gas detection method comprising;

a) providing a circuit operatively connected to a source of power and containing an active element and a reference element arranged in the circuit for separate current flow through the active and reference elements, the active element changing in temperature and resistance in the presence of the gas being detected;

b) supplying power, using pulse modulation, separately to the active and reference elements;

c) monitoring the resistances of the active and reference elements, the resistances being proportional to the temperatures of the active and reference elements; and d) using the resistances of the active and reference elements to control the pulse modulation to maintain a constant temperature on the active and reference elements.

20. The gas detection method of claim 19, further including translating the difference in power supplied to the active and reference elements needed to maintain constant temperature on the active elements and reference into an output proportional to the concentration of gas being detected.

21. The gas detection method according to claim 20, further including substantially reducing power applied to the active element while continuing to apply power to the reference element when there is sensed a rise in concentration of gas being detected above a predetermined level.

22. The gas detection method according to claim 21, further including determining the increase in power needed to maintain the reference element at a constant temperature as a measure of the concentration of the gas being detected.

23. A gas detector comprising:
   a) a circuit operatively connected to a source of applied voltage and containing an active element and a reference element arranged in the circuit for separate current flow through the active and reference elements, the active element changing in temperature and resistance in the presence of the gas being detected; and
   b) a controller operatively connected to the circuit for controlling the supply of power, using pulse modulation, separately to the active and reference elements, the controller also being connected in monitoring relation to the active and reference elements to read voltages associated with the active and reference elements, and the controller using the ratio between the voltage associated with the active element and the applied voltage and the ratio between the voltage associated with the reference element and the applied voltage to control the pulse modulation to maintain a constant temperature on the active and reference elements.

24. The gas detector of claim 23, wherein the controller maintains a constant ratio between the voltage associated with the active element and the applied voltage and a constant ratio between the voltage associated with the reference element and the applied voltage to maintain constant resistances and temperatures of the active and reference elements.

25. The gas detector of claim 23, wherein the controller compares each of the ratios to a predetermined target and adjusts the pulse modulation to adjust the supply of power to the respective ones of the active and reference elements to maintain the ratios constant.

26. The gas detector of claim 25, wherein the controller uses changes in the pulse modulation to maintain the ratios constant to provide information on changes in concentration of the gas being detected.

27. The gas detection method of claim 26, including comparing each of the ratios to a predetermined target and adjusting the pulse modulation to adjust the supply of power to the respective ones of the active and reference elements to maintain the ratios constant.

28. The gas detection method of claim 25, including maintaining a constant ratio between the voltage associated with the active element and the applied voltage and a constant ratio between the voltage associated with the reference element and the applied voltage to maintain constant resistances and temperatures of the active and reference elements.

29. A gas detection method comprising:
   a) providing a circuit operatively connected to a source of applied voltage and containing an active element and a reference element arranged in the circuit for separate current flow through the active and reference elements, the active element changing in temperature and resistance in the presence of the gas being detected;
   b) supplying power, using pulse modulation, separately to the active and reference elements;
   c) reading voltages associated with the active and reference elements; and
   d) using the ratio between the voltage associated with the active element and the applied voltage and the ratio between the voltage associated with the reference element and the applied voltage to control the pulse modulation to maintain a constant temperature on the active and reference elements.

30. The gas detection method of claim 29, including utilizing changes in the pulse modulation to maintain the ratios constant to provide information on changes in concentration of the gas being detected.

* * * * *